United States Patent
Liu et al.

(10) Patent No.: US 9,468,416 B2
(45) Date of Patent: Oct. 18, 2016

(54) QUALITY-CONTROL JIG FOR USE WITH RADIOTHERAPY APPARATUS

(71) Applicant: University of Florida Research Foundation, Incorporated, Gainesville, FL (US)

(72) Inventors: Chihray Liu, Gainesville, FL (US); Guanghua Yan, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 224 days.

(21) Appl. No.: 14/295,264

(22) Filed: Jun. 3, 2014

(65) Prior Publication Data

US 2015/0343239 A1  Dec. 3, 2015

(51) Int. Cl.
*A61B 6/04* (2006.01)
*A61B 6/08* (2006.01)
*A61N 5/10* (2006.01)
*G09B 23/28* (2006.01)
*A61B 6/00* (2006.01)

(52) U.S. Cl.
CPC ............ *A61B 6/584* (2013.01); *A61B 6/0492* (2013.01); *A61B 6/547* (2013.01); *A61B 6/589* (2013.01); *A61N 5/1049* (2013.01); *A61B 6/08* (2013.01); *A61N 5/1075* (2013.01); *A61N 2005/1076* (2013.01); *G09B 23/286* (2013.01)

(58) Field of Classification Search
CPC ............ A61B 6/00; A61B 6/02; A61B 6/04; A61B 6/0492; A61B 6/08; A61B 6/44; A61B 6/54; A61B 6/545; A61B 6/547; A61B 6/58; A61B 6/582; A61B 6/583; A61B 6/584; A61B 6/589; A61N 5/10; A61N 5/103; A61N 5/1048; A61N 5/1049; A61N 5/1075; A61N 2005/105; A61N 2005/1061; A61N 2005/1076; A61N 205/1092; G09B 23/00; G09B 23/06; G09B 23/22; G09B 23/28; G09B 23/286

See application file for complete search history.

(56) References Cited

U.S. PATENT DOCUMENTS

| | | | |
|---|---|---|---|
| 4,618,978 A | * | 10/1986 | Cosman ............ A61B 6/08 324/309 |
| 7,313,222 B2 | * | 12/2007 | Carlsson ............ A61N 5/1049 378/205 |
| 2009/0190723 A1 | | 7/2009 | Jang |
| 2010/0303210 A1 | * | 12/2010 | Beaumont ............ A61N 5/1048 378/207 |
| 2014/0016759 A1 | | 1/2014 | Ngar |
| 2014/0046601 A1 | | 2/2014 | Carlsson |

FOREIGN PATENT DOCUMENTS

| | | |
|---|---|---|
| CN | 203436699 | 2/2014 |
| FR | 2946243 | 12/2010 |

OTHER PUBLICATIONS

International Search Report mailed Aug. 19, 2015 for PCT/US15/33877 filed Jun. 3, 2015.
Written Opinion mailed Aug. 19, 2015 for PCT/US15/33877 filed Jun. 3, 2015.

* cited by examiner

*Primary Examiner* — Anastasia Midkiff
(74) *Attorney, Agent, or Firm* — Fleit Gibbons Gutman Bongini & Bianco PL; Paul D. Bianco; Lourdes Perez

(57) ABSTRACT

A jig for calibrating an image-guided radiotherapy apparatus is disclosed. The jig includes a ball bearing and a three-axis positioner. Once the ball bearing has been moved to the calculated radiation isocenter of the apparatus, other calibration procedures can be performed by directing light onto the jig.

9 Claims, 6 Drawing Sheets

QUALITY-CONTROL JIG FOR USE WITH RADIOTHERAPY APPARATUS

BACKGROUND OF THE INVENTION

The invention relates to radiotherapy, and more particularly relates to image-guided radiotherapy ("IGRT"). In its most immediate sense, the invention relates to a quality-control jig for use with IGRT apparatus.

In IGRT apparatus, two instruments are mounted upon a rotatable gantry. One of these is a linear accelerator (a "linac"). The linac produces a beam of high-energy radiation (the "treatment beam") used to destroy tumor tissue inside the patient's body. The other is an imager (which is usually but not necessarily a cone-beam computed-tomography imager). This produces a lower-energy beam of radiation (the "imaging beam") used to create a three-dimensional image of the patient's body region in which the patient's tumor is located. The linac's treatment beam and the imager's imaging beam are at right angles to each other.

Before a patient is imaged and subjected to radiation therapy, it is necessary to make sure that the IGRT apparatus is properly calibrated. This is because IGRT apparatus operates neither with theoretical perfection nor with absolute repeatability.

For these reasons, radiation technicians routinely carry out quality-control procedures on IGRT apparatus before patients are imaged and subjected to radiation therapy. This enables the technicians to monitor the actual performance of the IGRT apparatus and to make sure that the apparatus is properly calibrated. However, such procedures are time-consuming and complicated.

It would be advantageous to provide a jig that would make it easier to carry out quality-control procedures on IGRT apparatus, and to make it possible to carry out those procedures more quickly.

Objects of the present invention are to provide a jig that facilitates and speeds the performance of quality-control procedures on IGRT apparatus.

The invention proceeds from the realization that a ball bearing that is used to carry out a common quality-control procedure can be incorporated as a detachable part of a jig that can be used to check other apparatus parameters by shining light on the jig.

In accordance with the invention, a jig has an elongated stylus with a proximal end and a distal end. The proximal end of the stylus is secured to a three-axis positioner.

A ball bearing is provided, as is a ball bearing cap that is secured to the ball bearing and adapted to fit over the distal end of the stylus to detachably mount the ball bearing thereto. A pointer having a distal tip is provided, as is a pointer cap that is secured to the pointer and adapted to fit over the distal end of the stylus to detachably mount the pointer thereto. The ball bearing, the ball bearing cap, the pointer, and the pointer cap are all dimensioned such when the pointer cap is mounted to the distal end of the stylus, the distal tip of the pointer has the same location as does the center of the ball bearing when the ball bearing cap is mounted to the distal end of the stylus.

A flat plate is provided, as are means for fixing the plate to the stylus in such a manner that the pointer will cast a shadow on the plate when a light is directed onto the pointer from a direction normal to the plate.

This jig makes it easy to carry out many commonly-performed quality-control quickly and efficiently. Once the positioner has been used to place the ball bearing at the calculated radiation isocenter of the IGRT apparatus, measurements of other apparatus parameters can be carried out relative to the known position of the radiation isocenter by directing light onto the jig.

Advantageously, the fixing means is adapted to fix the plate to the stylus at a 0° orientation, a 90° orientation, a 180° orientation, and a 270° orientation. This allows the jig to be conveniently reconfigured for use at four gantry positions. Likewise advantageously, an axially-elongated hollow phantom is provided. The phantom is detachably securable to the positioner in a manner that the stylus extends along the axis of the phantom and has surface markings indicating locations that are axially aligned with the center of the ball bearing and that are also rotationally aligned with gantry orientations of 0°, 90°, and 270°. This makes it possible to align the lasers used to position the patient. Additionally, four infrared-reflecting markers are mounted on the anterior surface of the phantom. The locations of these markers are known precisely, making it possible to calibrate and quality-control optical tracking equipment such as is conventionally used with IGRT apparatus.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
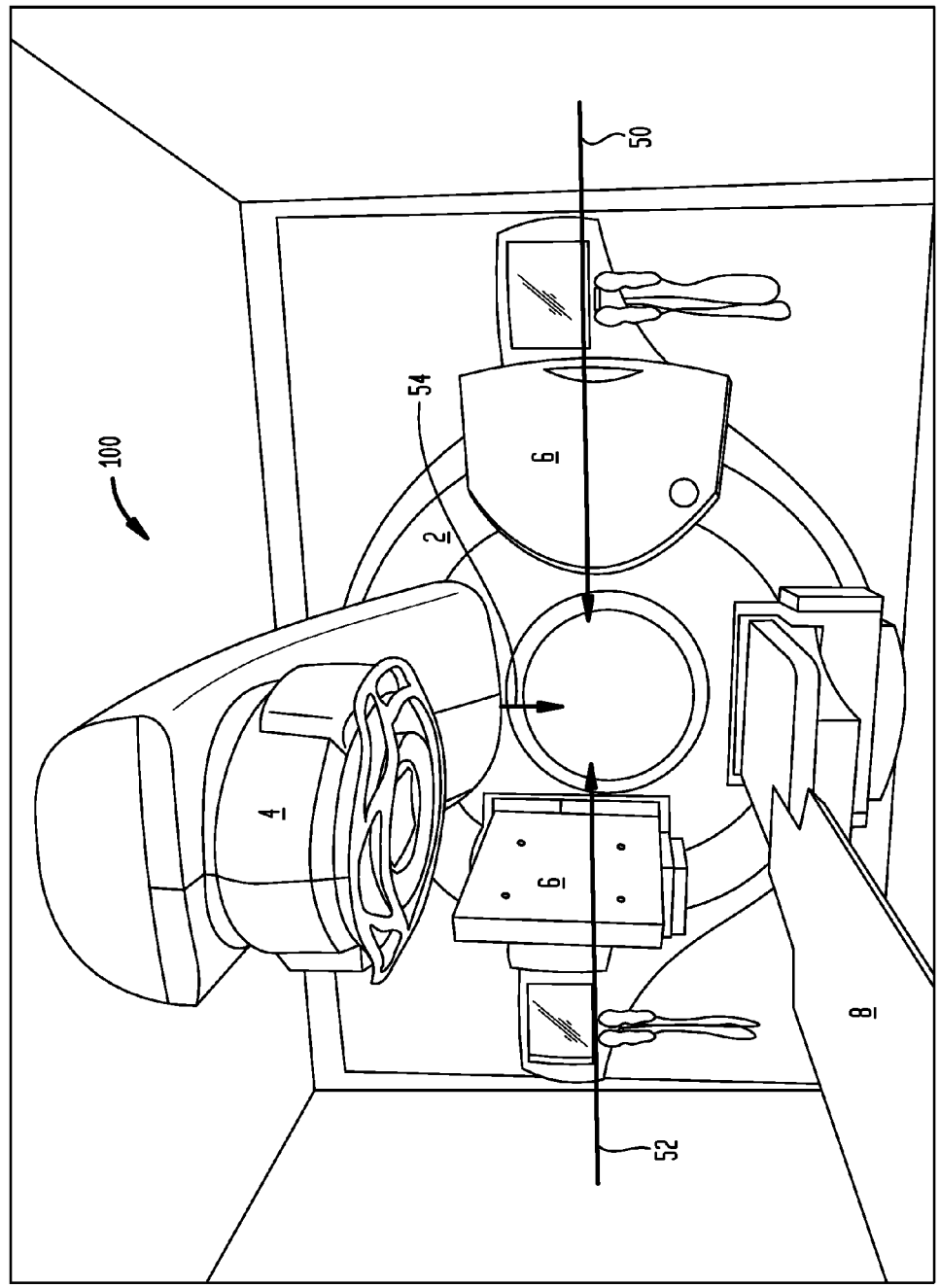
FIG. 1 shows an image-guided radiation therapy apparatus.

The Figures herein are not necessarily to scale; various components may be enlarged or reduced for clarity of illustration. The same element is always indicated by the same reference numeral in all the Figures.

FIG. 1 shows a conventional image-guided radiation therapy ("IGRT") apparatus generally indicated by reference numeral 100. A toroidal gantry 2 is supported to rotate in a vertical plane. A linac 4 is attached to the gantry 2, as is an imager 6. (In this example, the imager 6 is a cone-beam computed tomography imager, but this is not required. Another imaging device, such as an X-ray apparatus, can be used instead.)

The IGRT apparatus 100 has a patient table 8; in use, a patient (not shown) is supported on the table 8. Initially, the table 8 and the imager 6 are adjusted so that the imager 6 is aimed at the body region where a tumor (likewise not shown) is located. In an initial imaging phase, the gantry 2 is rotated while the imager 6 is operated to acquire image data from the patient. Once image data of the patient have been acquired through 360° of rotation of the gantry 2, a three-dimensional image is reconstructed and registered. In this image, the location of the tumor within the body is accurately identified. Then, in a subsequent treatment phase, the gantry 2 is rotated through 360 degrees while the linac 4 is operated in accordance with the registered image information. Radiation from the linac 4 necrotizes the tumor.

Before carrying these steps out on a patient, it is necessary to carry out quality-control procedures to make sure that the IGRT apparatus 100 is properly calibrated. This is because the IGRT apparatus 100 is not mechanically perfect and does not operate with absolute repeatability. For example, the parts of the gantry 2, the linac 4, and the imager 6 are not absolutely rigid and all mechanical parts are subject to wear. As a result, the various parts of the IGRT apparatus 100 flex during rotation of the gantry 2. This flexure makes points in the patient's image appear to move with rotation of the gantry 2. To minimize flexure-caused distortion of the image reconstructed from data acquired by the imager 6, the flexure is conventionally measured at various orientations of the gantry 2 and taken into account during image reconstruction.

To do this, in one universally-practiced quality control procedure, a ball bearing is moved to the geometric center of the radiation field of the linac 4. The ball bearing is then imaged by the linac 4 at four orientations of the linac 4 (i.e. at gantry orientations 0°, 90°, 180°, and 270°). This localizes the ball bearing within the radiation field of the linac 4, and the ball bearing can then be moved to the computed radiation isocenter of the IGRT apparatus 100. After this has been done, the position of the ball bearing is measured in the coordinate system of the imager 6 throughout the range of orientations of the gantry 2, thereby creating a so-called "Flex Map" that is used when an image is reconstructed from data acquired using the imager 6.

This is not the only quality-control procedure applicable to calibration of IGRT apparatus; others are used as well. These will be explained below in connection with the following description of a preferred embodiment of the invention.

Figure 2:
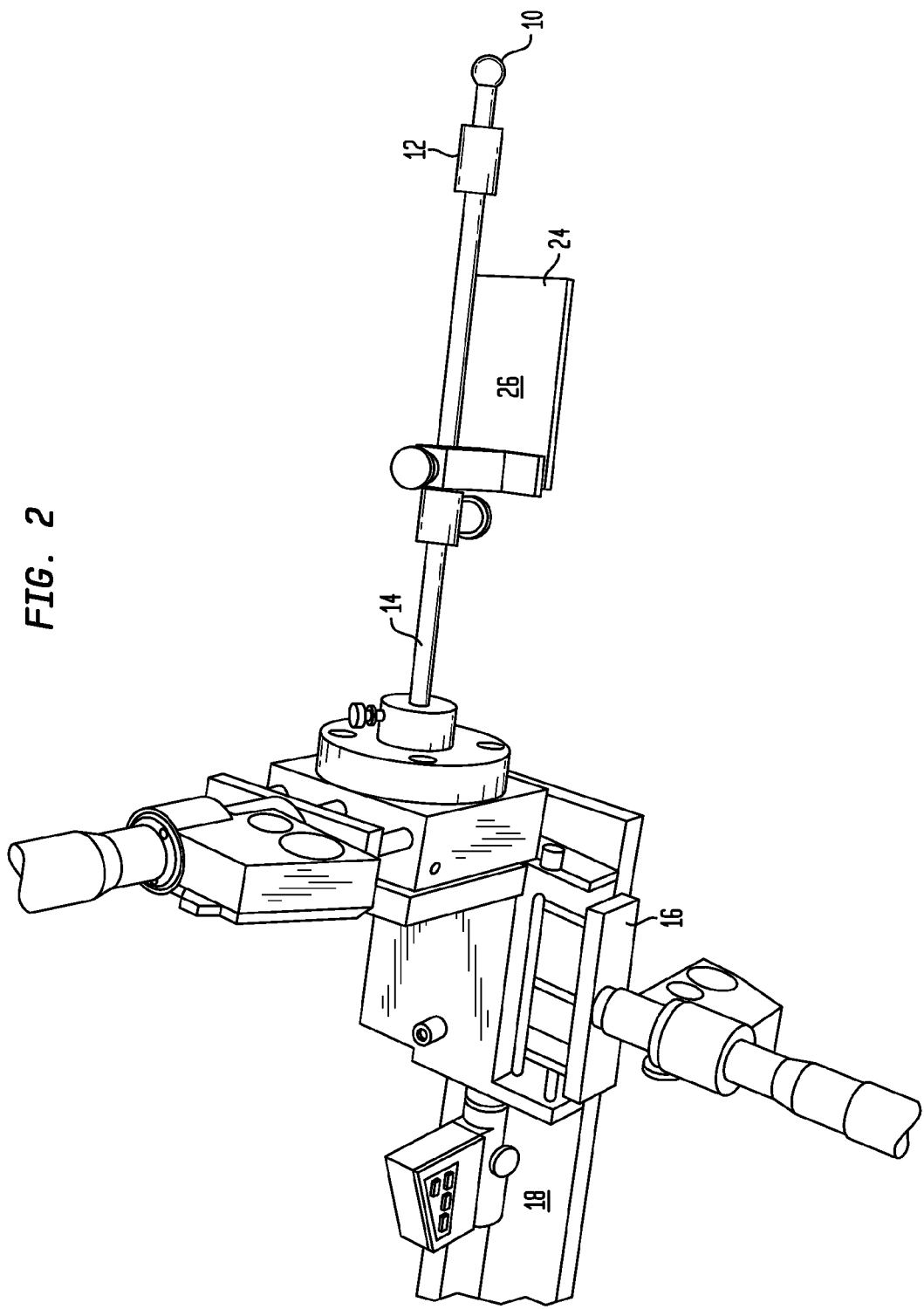
FIG. 2 shows a preferred embodiment of the invention, configured to determine the radiation isocenter of an image-guided radiation therapy apparatus with which it is used.

Referring now to FIG. 2, a ball bearing 10 is mounted to a ball bearing cap 12. The ball bearing cap 12 is sized to fit over the distal end of a stylus 14, and the proximal end of the stylus 14 is secured to a three-axis positioner 16. The positioner 16 is mounted on a base 18.

Initially, the ball bearing cap 12 is fit over the distal end of the stylus 14, the base 18 is placed upon the table 8, and the ball bearing 10 is imaged by the linac 4 at the 0°, 90°, 180°, and 270° orientations of the gantry 2. The radiation isocenter of the IGRT apparatus 100 is then computed, and the ball bearing 10 is then moved to that computed position by adjustment of the positioner 16 along directions parallel to the table 8.

Once the ball bearing 10 has been moved to the computed radiation isocenter of the IGRT apparatus 100, it is possible to check whether the height of the table 8 is proper. This can be done by measuring the distance between the ball bearing 10 and the table 8 and comparing that measured distance with the distance that is expected to be present.

Figure 3:
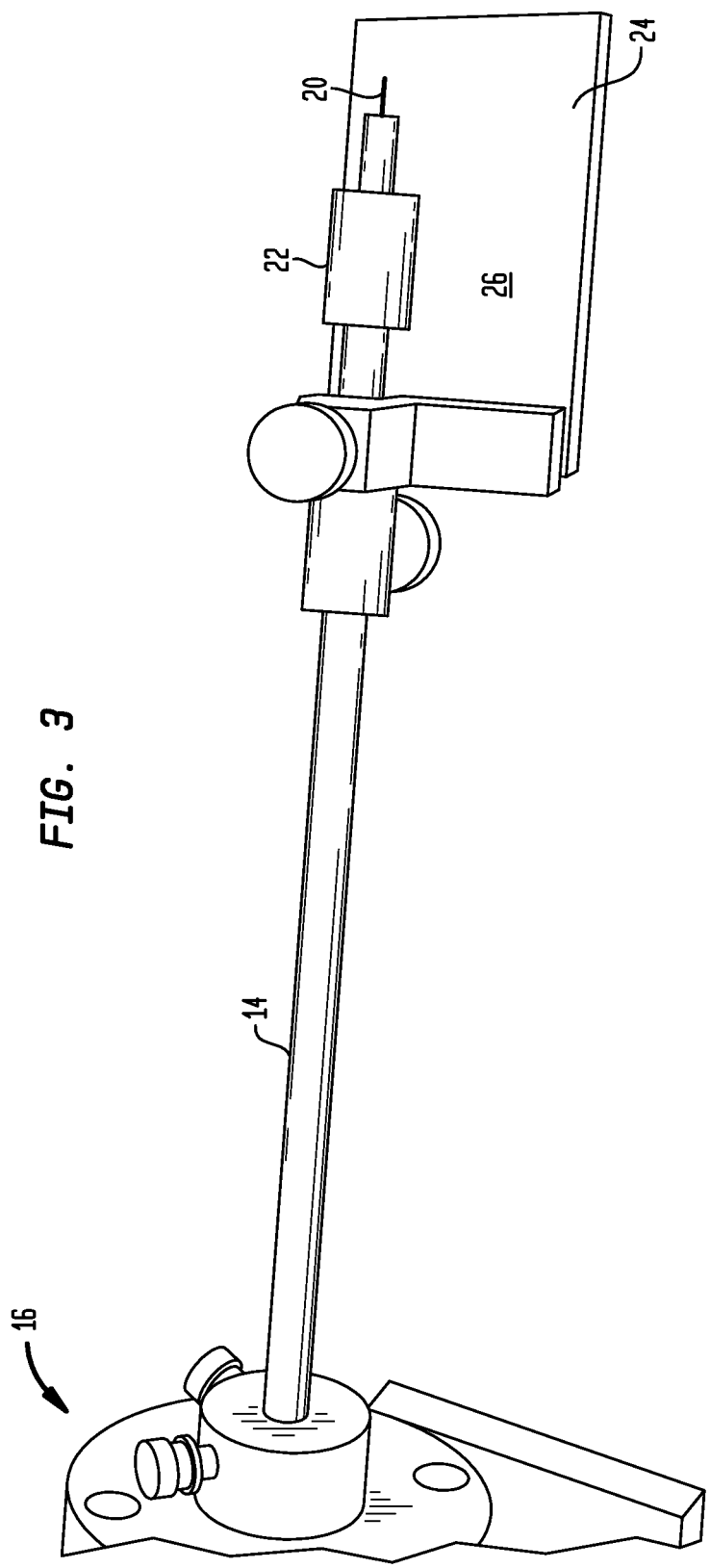
FIG. 3 shows a portion of the preferred embodiment of the invention, configured to determine the mechanical isocenter of an image-guided radiation therapy apparatus with which it is used.
Figure 4:
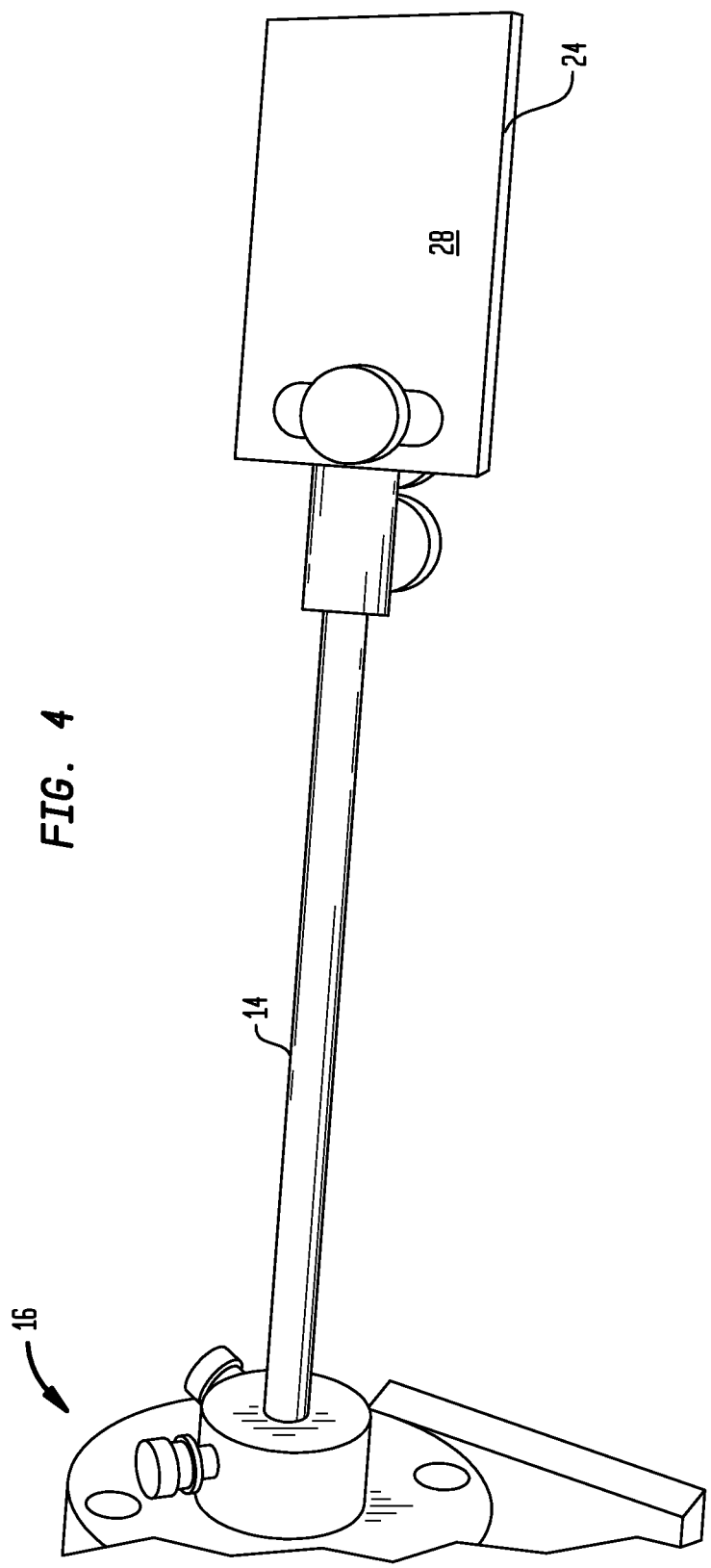
FIG. 4 shows a portion of the preferred embodiment of the invention, configured to check the calibration of an optical distance indicator in the linac of an image-guided radiation therapy apparatus with which it is used.

The preferred embodiment of the invention makes it possible to check the relationship between the radiation isocenter of the IGRT 100 and the mechanical isocenter of the IGRT apparatus 100. To do this, the ball bearing cap 12 is detached from the distal end of the stylus 14 and replaced with an assembly made up of a pointer 20 and a pointer cap 22 that is secured to the pointer 20 (FIG. 3). The pointer cap 22, like the ball bearing cap 12, fits over the distal end of the stylus 14. And, importantly, the dimensions of the ball bearing 10, the ball bearing cap 12, the pointer 20, and the pointer cap 22 are chosen so that when the pointer cap is mounted to the distal end of the stylus 14, the distal tip of the pointer 20 is located where the center of the ball bearing 10 is located when the ball bearing cap 12 is mounted to the distal end of the stylus 14.

Advantageously although not necessarily, two different ball bearings 10 are provided, each being mounted on a cap 12 so as to be mountable on the stylus 14. The ball bearings 10 and their associated caps 12 are dimensionally identical, but the two ball bearings 10 are of different densities; one has a higher density than the other. The higher density ball bearing 10 is used as stated above to compute the radiation isocenter of the IGRT apparatus 100. In a subsequent step, the higher density ball bearing 10 and its attached cap 12 can be removed from the stylus 14 and replaced by the lower density ball bearing 10 and its attached cap 12. Then, an image of the lower density ball bearing 10 can be acquired using the imager 6 (which is typically rotated through 360° in order to acquire the image). The displacement between the radiation isocenter and the isocenter of the imager 6 is then measured to determine whether this displacement is within specifications (it should typically be less than 2 mm). Since the radiation isocenter is sometimes referred to as the "MV isocenter" and the isocenter of the imager 6 is sometimes referred to as the "KV isocenter", this quality control measure is referred to as a "KV and MV isocenter coincidence check".

Each of the linac 4 and the imager 6 has a light (not specifically shown) at its radially inward face. And, a flat plate 24 is mounted to the stylus 14. As can be seen in FIG. 3, the flat plate 24 is so located that the pointer 20 casts a shadow on a ruled side 26 of the plate 24 when light is directed upon the pointer 20. (The ruled side 26 bears a Cartesian coordinate system calibrated in millimeters so that the precise position of the shadow cast by the pointer 20 can be noted. The ruled side 26 can be permanently ruled or a ruled piece of paper can be detachably secured to it.)

Thus, when a light from either the linac 4 or the imager 6 is directed upon the pointer 20, the pointer 20 casts a shadow onto the ruled side 26 of the plate 24 and the position of that shadow indicates the actual position of the linac 4 or imager 6 (as the case may be). This provides a way to track the mechanical isocenter of the IGRT apparatus 100; at various positions of the gantry 2, the position of the tip of the shadow on the ruled side 26 of the flat plate 24 is noted. Advantageously, the plate 24 is so mounted to the stylus 14 that the plate can be rotated to, and fixed in, positions corresponding to the 0°, 90°, 180°, and 270° orientations of the gantry 2. Thus, if the gantry 2 is set to the 0° orientation (i.e. with the linac 4 facing directly downwardly), the plate 24 will be rotated so that the ruled side 26 faces up; if the gantry 2 is set to the 270° orientation (i.e. with the linac 4 facing left) the plate 24 will be rotated so that the ruled side 26 faces right. A review of the variation in the position of the shadow tip at these gantry orientations makes it possible to determine whether the mechanical performance of the gantry 2 is within applicable specifications.

The linac 4 will typically have an optical distance indicator ("ODI", not shown) that measures distance from the linac 4 to the patient to be treated. The operation of the linac 4 can be checked by rotating the plate 24 so that its non-ruled side 28 faces the linac 4, aiming the linac 4 at the non-ruled side 28 so that the ODI directs light thereon, and checking to see if the distance measured by the ODI is within the tolerance required.

Figure 5:
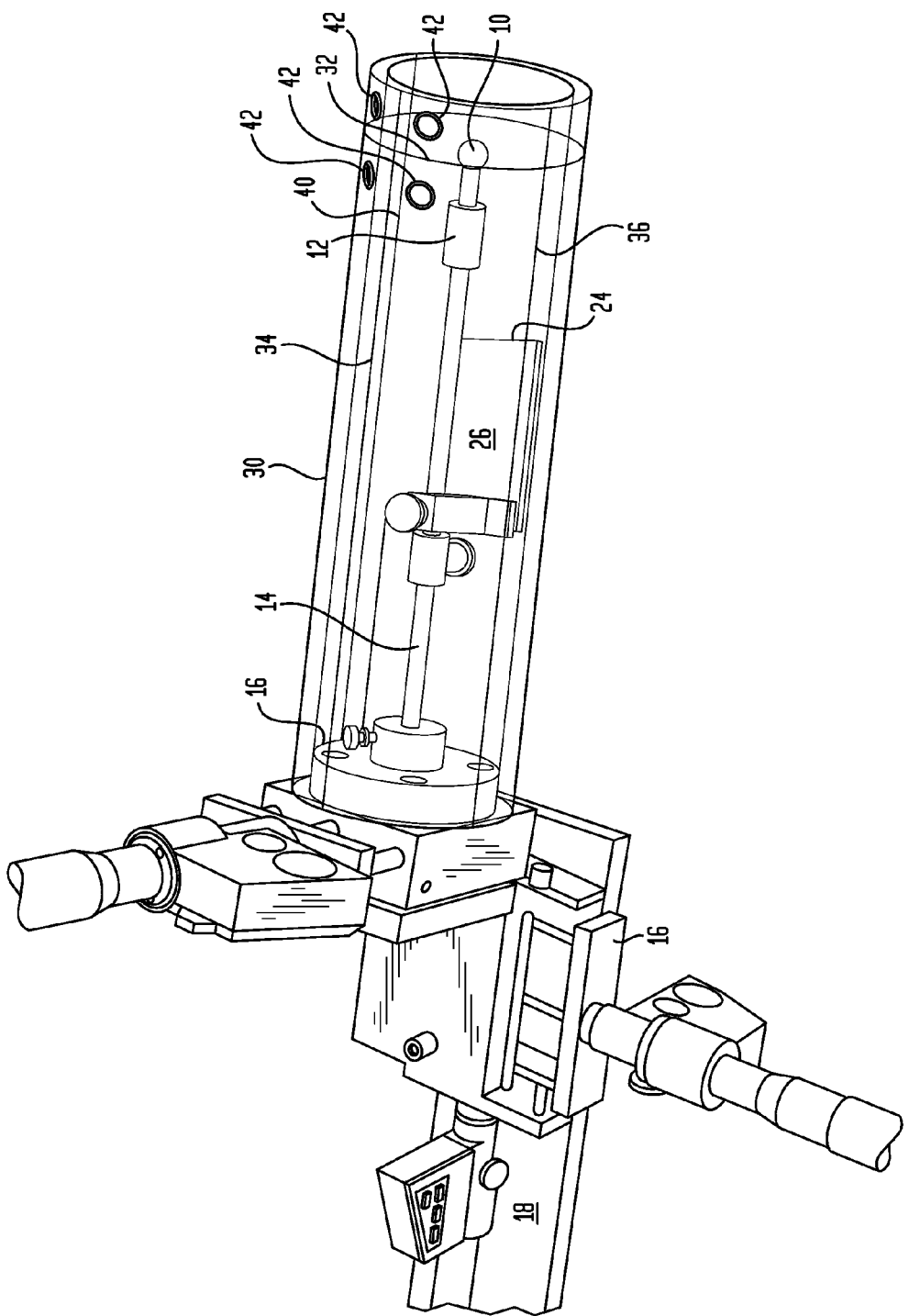
FIG. 5 is a perspective view of the preferred embodiment of the invention with a phantom mounted on it.
Figure 6:
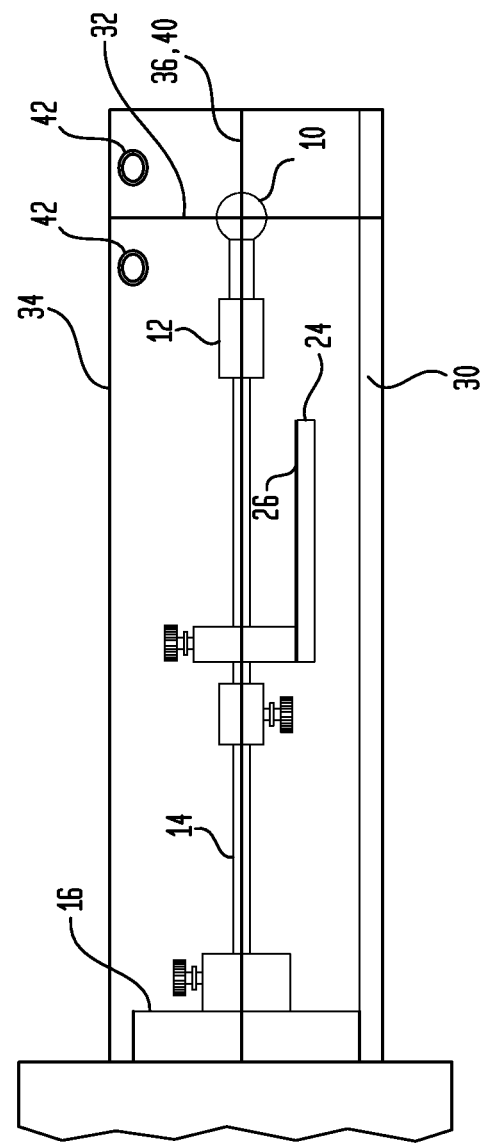
FIG. 6 is a side view of the preferred embodiment of the invention with the phantom mounted on it.

Conventionally, a room in which an IGRT apparatus is installed has a laser system that requires alignment. This is schematically illustrated in FIG. 1, which shows laser beams 50, 52, and 54 that are projected toward the radiation isocenter of the IGRT apparatus 100 from lasers (not shown) that are mounted in the room in which the IGRT apparatus 100 is located. In order to make sure this laser system is properly aligned, an axially-elongated cylindrical acrylic phantom 30 (FIGS. 5 and 6) is threaded onto the positioner 16 in such a manner that the stylus 14 extends along the axis of the phantom 30.

The phantom 30 has surface markings indicating locations that are axially aligned with the center of the ball bearing 10 and that are also rotationally aligned with gantry orientations of 0°, 90°, and 270°. The circular line 32 is axially aligned with the center of the ball bearing 10. Each of surface lines 34, 36, and 40 is parallel to the stylus 14. The line 34 is on the top of the phantom 30, at a position corresponding to a 0° orientation of the gantry 2, the line 36 is on the side of the phantom 30, at a position corresponding to a 90° orientation of the gantry 2, and the line 40 is on the other side of the phantom 30, at a position corresponding to a 270° orientation of the gantry 2. Thus, the surface of the phantom 30 has three points of intersection (one being at the intersection of lines 32 and 34, another being at the intersection of lines 32 and 36, and the third being at the intersection of lines 32 and 40).

Once the ball bearing 10 has been moved to the computed radiation isocenter, the phantom 30 can be mounted to the positioner 16 (as by being threaded onto it). The room lasers can then be calibrated or checked by turning them on and seeing how closely the beams 50, 52, and 54 are projected to these three points of intersection.

Four infrared-reflecting spherical markers 42 are mounted on the anterior top surface of the phantom 30. Each marker 42 is 1.2 cm in diameter. The four markers 42 form a 5 cm by 5 cm square centered on the center of the ball bearing 10. The coordinates of the four markers 42 are precisely known, which enables the calibration and quality control of optical tracking equipment such as is conventionally used with IGRT apparatus.

Although a preferred embodiment has been described above, the scope of the invention is determined only by the following claims:

The invention claimed is:

1. A quality-control jig for use with an image-guided radiotherapy apparatus, comprising:
   a. an elongated stylus having a proximal end and a distal end;
   b. a three-axis positioner operatively secured to the proximal end of the stylus;
   c. a first ball bearing having a center;
   d. a first ball bearing cap secured to the ball bearing and adapted to fit over the distal end of the stylus to detachably mount the first ball bearing thereto;
   e. a pointer having a distal tip;
   f. a pointer cap secured to the pointer and adapted to fit over the distal end of the stylus to detachably mount the pointer thereto, the first ball bearing, the first ball bearing cap, the pointer, and the pointer cap being dimensioned such that when the pointer cap is mounted to the distal end of the stylus, the distal tip of the pointer has the same location as does the center of the first ball bearing when the first ball bearing cap is mounted to the distal end of the stylus;
   g. a flat plate; and
   means for fixing the plate to the stylus in such a manner that the pointer will cast a shadow on the plate when light is directed onto the pointer.

2. The jig of claim 1, wherein said fixing means is adapted to fix the plate to the stylus at a 0° orientation, a 90° orientation, a 180° orientation, and a 270° orientation.

3. The jig of claim 1, further comprising an axially-elongated hollow phantom, the phantom
   a. being detachably securable to the positioner in a manner that the stylus extends along the axis of the phantom,
   b. having surface markings indicating locations that are axially aligned with the center of the ball bearing and that are also rotationally aligned with gantry orientations of 0°, 90°, 180° and 270°, and
   having four infrared-reflecting markers mounted on its anterior top surface, the markers being arranged in a square centered on the center of the ball bearing.

4. The jig of claim 1, further including a second ball bearing and a second ball bearing cap, the first and second ball bearings having identical external dimensions and different densities and the first and second ball bearing caps having identical external dimensions.

5. A method of calibrating an image-guided radiotherapy apparatus, comprising:
   a. obtaining a jig that includes a detachable ball bearing cap;
   b. placing the jig on a table of an image-guided radiotherapy apparatus;
   c. using the jig to move the ball bearing to the radiation isocenter of the image-guided radiotherapy apparatus;
   d. removing the ball bearing cap and replacing it with an assembly made up of a pointer and a pointer cap; and
   e. performing a calibration procedure on the radiotherapy apparatus by directing light onto the jig.

6. The method of claim 5, wherein the calibration procedure comprises measuring a mechanical isocenter of the apparatus.

7. The method of claim 5, wherein the apparatus has an optical distance indicator and the calibration procedure comprising calibrating the optical distance indicator.

8. The method of claim 5, wherein the calibration procedure comprises mounting a phantom on the jig and using the phantom to measure alignment of room lasers with the radiation isocenter of the image-guided radiotherapy apparatus.

9. The method of claim 8, wherein optical tracking equipment is provided with the apparatus and further comprising the step of using the phantom to calibrate the optical tracking equipment.

* * * * *